United States Patent [19]

De Wind et al.

[11] Patent Number: 5,695,765

[45] Date of Patent: Dec. 9, 1997

[54] MUTANT PSEUDORABIES VIRUS, AND VACCINES CONTAINING THE SAME

[75] Inventors: Niels De Wind, Amsterdam; Maria Madalene Van Zijl, Utrecht; Arnold Leonard Jozef Gielkens, Lelystad; Antonius Jozef Maria Berns, Spaarndam, all of Netherlands

[73] Assignee: Stichting Voor de Technische Wetenschappen, Utrecht, Netherlands

[21] Appl. No.: 378,097

[22] Filed: Jan. 25, 1995

Related U.S. Application Data

[63] Continuation of Ser. No. 834,569, Mar. 30, 1992, abandoned.

[30] Foreign Application Priority Data

Aug. 17, 1989 [NL] Netherlands ............................ 8902087

[51] Int. Cl.$^6$ ...................... A61K 39/245; A61K 39/295; C12N 7/01; C12N 7/04
[52] U.S. Cl. .................................. 424/199.1; 435/235.1; 435/172.3; 435/236; 424/205.1; 424/229.1
[58] Field of Search .................................. 435/235.1, 236, 435/172.3, 320.1; 424/199.1, 205, 229.1; 935/65, 32, 57

[56] References Cited

FOREIGN PATENT DOCUMENTS 9141458  5/1985  European Pat. Off. .
WO89/01040  2/1989  WIPO .

OTHER PUBLICATIONS

Van Zijl et al. J. Virol. 62(6):2191–95 1988.
Thomsen, D.R. et al. Gene, vol. 57, pp. 261–265, 1987.
"Deletions in the Genomes of Pseudorabies Virus Vaccine Strains and Existence of Four Isomers of the Genomes", Journal of Virology, vol. 49, No. 3, Mar. 1984, pp. 970–979, copyright 1984, by American Society for Microbiology.

"Pseudorabies Virus Avirulent Strains Fail to Express a Major Glycoprotein", Journal of Virology, vol. 56, No. 1, Oct. 1985, pp. 307–311, copyright 1985 by American Society for Microbiology.

"Herpes Simplex Virus 1 Protein Kinase Is Encoded by Open Reading Frame US3 Which Is Not Essential for Virus Growth in Cell Culture" Journal of Virology, vol. 61, No. 5, Sep. 1987, pp. 2896–2901, copyright 1987 by American Society for Microbiology.

"Construction and Characterization of Deletion Mutants of Pseudorabies Virus: a New Generation of Live Vaccines", J. gen. Virol, vol. 68, 1987, pp. 523–534, by W. Quint et al.

"Deletions in Vaccine Strains of Pseudorabies Virus and Their Effect on Synthesis of Glycoprotein gp63", Journal of Virology, vol. 60, No. 3, Dec. 1986, pp. 1166–1169, copyright 1986, by American Society for Microbiology.

Primary Examiner—Mary E. Mosher
Attorney, Agent, or Firm—Young & Thompson

[57] ABSTRACT

The invention relates to a pseudorabies virus (PRV) not found in nature and having a genome containing a mutation in the protein kinase gene region and/or in the 28K gene region. The mutation is e.g. a nucleic acid substitution, deletion, insertion or inversion, or a combination thereof. The mutations are introduced, by genetic engineering techniques, into the genome of a naturally occuring PRV, preferably NIA-3. Insertions may be nucleic acid sequences encoding antigenic polypeptides characteristic of a pathogen found in pigs. The invention also relates to vaccines containing a pseudorabies virus according to the invention, and to a process for preparing such vaccines.

13 Claims, 6 Drawing Sheets fig-1

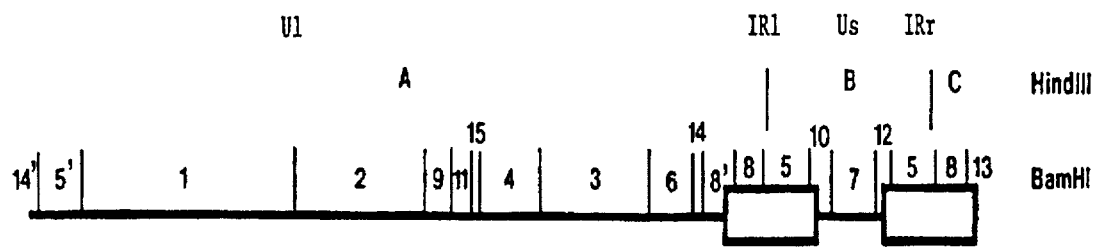

fig-2.1

```
        IR  ←
    1   GGGCGGCGGCGCCCCCGTCGCGGTCGAGAACCACCGCCGCCGTCACCGCCGCCTCCCACCCGATGTGATATCGCG    75
                                       →
   76   GCACGCCGGCCGTCCCGGCGCTCATTCACACCGCACCCGTTCGCCCACGTCCCCGCGGGCAAGCACGCACACACC   150

151   CGGTCGCGCATCATGCTGGCGATGTGGAGATGGGTCACCAAGAGGTCGCGGCTCCGCCGAGGCCACGCCCATCTT   225
                      M L A H W R W V T K R S R L R R G H A H L
                                       →
  226   GGGGGAAATAAAGGAGTCCGGGGAATTTGTTCCTTATACCTTGCCGGGCTCAGCAGGGGGTTGTCGCGCGTCCAC   300
        G G N K G V R G I C S L Y L A G L S R G L S R V H

301   GCCCAGCGCTCGCACGCAGCAACAATGGCCGACGCCGGAATCCCCGACGAGATCCTGTACTCGGACATCAGCGAC   375
        A Q R S H A A T M A D A G I P D E I L Y S D I S D
                          ↓
  376   GACGAGATCATCATCGACGGCGACGGCGACGGCGACAGCAGCGGGGACGAGGACGACGATGACGGGGGGCTGACG   450
        D E I I I D G D G D G D S S G D E D D D D G G L T

451   CGGCAGGCCGCGTCGCGCATCGCCACGGACCTGGGCTTCGAGGTGCTGCAGCCCCTGCAGTCGGGCTCGGAGGGC   525
        R Q A A S R I A T D L G F E V L Q P L Q S G S E G
```

Fig-2.2

```
526  CGCGTCTTCGTGGCCCGCCGGCCCGGCGAGGCGGACACGGTGGTGCTGAAGGTGGGCCAGAAGCCCTCGACGCTG  600
     R  V  F  V  A  R  R  P  G  E  A  D  T  V  V  L  K  V  G  Q  K  P  S  T  L

601  ATGGAGGGCATGCTGCTGAAGCGCCTGGCCCACGATAACGTCATGAGCCTGAAGCAGATGCTCGCCCGGGGCCCG  675
     M  E  G  H  L  L  K  R  L  A  H  D  N  V  M  S  L  K  Q  M  L  A  R  G  P

676  GTGACGTGCCTGGTCCTGCCGCACTTTCGGTGCGATCTGTACAGCTACCTGACCATGCGGGACGGGCCGCTGGAC  750
     V  T  C  L  V  L  P  H  F  R  C  D  L  Y  S  Y  L  T  M  R  D  G  P  L  D

751  ATGCGCGACGCCGGGCGCGTGATCCGGTCCGTGCTCCGCGGGCTCGCCTACCTGCACGGGATGCGCATCATGCAC  825
     M  R  D  A  G  R  V  I  R  S  V  L  R  G  L  A  Y  L  H  G  M  R  I  M  H

826  CGCGACGTCAAGGCGGAGAACATCTTCCTCGAGGACGTGGACACGGTGTGCCTGGGGGACCTCGGGGCCGCGCGC  900
     R  D  V  K  A  E  N  I  F  L  E  D  V  D  T  V  C  L  G  D  L  G  A  A  R

901  TGCAACGTGGCGGCGCCCAACTTTTACGGGCTCGCCGGGACCATCGAGACCAACGCCCCCGAGGTGCTCGCGCGC  975
     C  N  V  A  A  P  N  F  Y  G  L  A  G  T  I  E  T  N  A  P  E  V  L  A  R

976  GACCGCTACGACACCAAGGTCGACGTCTGGGGCGCGGGGGTGGTGCTCTTCGAGACGCTGGCCTACCCCAAGACG  1050
     D  R  Y  D  T  K  V  D  V  W  G  A  G  V  V  L  F  E  T  L  A  Y  P  K  T

1051 ATCGCCGGCGGGGACGAGCCCGCGATCAACGGGGAGATGCACCTGATCGACCTCATCCGCGCCCTCGGGGTGCAC  1125
     I  A  G  G  D  E  P  A  I  N  G  E  M  H  L  I  D  L  I  R  A  L  G  V  H

1126 CCCGAGGAGTTCCCGCCCGACACGCGCCTCCGGAGCGAGTTCGTCCGGTACGCCGGGACCCACCGCCAGCCGTAC  1200
     P  E  E  F  P  P  D  T  R  L  R  S  E  F  V  R  Y  A  G  T  H  R  Q  P  Y

1201 ACGCAGTACGCGCGCGTGGCTCGCCTCGGGCTGCCCGAGACGGGGGCTTTCCTGATTTACAAGATGTTGACGTTT  1275
     T  Q  Y  A  R  V  A  R  L  G  L  P  E  T  G  A  F  L  I  Y  K  M  L  T  F

1276 GATCCCGTCCGCCGCCCTTCCGCTGATGAGATACTCAACTTTGGAATGTGGACCGTATAAAACGGCCCGGCTCCG  1350
     D  P  V  R  R  P  S  A  D  E  I  L  N  F  G  M  W  T  V  *

1351 AGCGGTAGGACACACACACACCTTTGCGCATCTCCACAGCTCAACAATGAAGTGG  1403
                                                     M  K  W
```

DNA-sequence of the protein kinase gene fig-3.1

```
1   CACGTGTAGCGAGCGAGCGAACGGGAGCGGGGCCCGCCCCCATCCGCCGCGCCCAGGAGAGGGGGGAGAGAGCGG   75
    H  V  *

76  GGGGTTGAGCGCGCCACGTGGTTGTGGGCTCGGACTTGTCACAATAAATGGGCCCCGGCGCGCCCGGGCGCACAC   150

151 AGCAGCCTTCCTCGTCTCCGCGTCTCTGCTGTTCCTCTCGTCGGTCTTCTCCCACTCCGCCGTCGCGAACGCGCT   225

226 CGCGCCATGGGGGTGACGGCCATCACCGTGGTCACGCTGATGGACGGGTCCGGGCGCATCCCCGCCTTCGTGGGC   300
         H  G  V  T  A  I  T  V  V  T  L  M  D  G  S  G  R  I  P  A  F  V  G

301 GAGGCGCACCCGGACCTGTGGAAGGTGCTCACCGAGTGGTGCTACGCGTCGCTGGTGCAGCAGCGGCGCGCCGCC   375
     E  A  H  P  D  L  W  K  V  L  T  E  W  C  Y  A  S  L  V  Q  Q  R  R  A  A

376 GACGAGGACACGCCGCGGCAACACGTGGTGCTGCGCTCCTCGGAGATCGCCCCCGGCTCGCTGGCCCTGCTGCCG   450
     D  E  D  T  P  R  Q  H  V  V  L  R  S  S  E  I  A  P  G  S  L  A  L  L  P

451 CGCGCCACGCGCCCCGTCGTGCGGACACGGTCCGACCCCACGGCGCCGTTCTACATCACCACCGAGACGCACGAG   525
     R  A  T  R  P  V  V  R  T  R  S  D  P  T  A  P  F  Y  I  T  T  E  T  H  E

526 CTGACGCGGCGCCCCCCGGCGGACGGCTCGAAGCCCGGGGAGCCCCTCCGTATCAGCCCGCCCCCGCGGCTGGAC   600
     L  T  R  R  P  P  A  D  G  S  K  P  G  E  P  L  R  I  S  P  P  P  R  L  D

601 ACGGAGTGGTCCTCCGTCATCAACGGGATCCAGTACCTGAACTCGGGGGCCCGGGGCACGGCCCCGATCCACCTG   675
     T  E  W  S  S  V  I  N  G  I  Q  Y  L  N  S  G  A  R  G  T  A  P  I  H  L

676 TGGATCCTGGGCGCCGCCGACCTCTGCGACCAGGTGCTCCTGGCCGCCTCCCGCAGCACCGCCGCCGGAGCCCCC   750
     W  I  L  G  A  A  D  L  C  D  Q  V  L  L  A  A  S  R  S  T  A  A  G  A  P

751 GGCGCCCCGACGGGCGCGCGCCTGACCCGGCGGCGGCCCGGGCTGACGGACGCCGACGCCCTGGACGTGATCGTC   825
     G  A  P  T  G  A  R  L  T  R  R  R  P  G  L  T  D  A  D  A  L  D  V  I  V
``` fig-3.2

```
 826 GCCGGGATCCCCGGCCACCCGCGCCATGTTCGCGCGGGTCCACAACCGCTCCTGGCGCCACGCCGGCGAGTGGACG  900
     A  G  I  P  A  T  R  A  H  F  A  R  V  H  N  R  S  W  R  H  A  G  E  W  T

901 GAGGCCCTGCATGCCCAGATCGTGACCCGGGGCGACGTGCGCCGGCGCCGGGGCGGGCGCGGCAACGGACGCGAG   975
     E  A  L  H  A  Q  I  V  T  R  G  D  V  R  R  R  R  G  G  R  G  N  G  R  E

976 CGCGCCCCGCGATGTACCATCTCCTAGACGGCAGGATCTCTCCGCATCCCCCACTCCCCCCAAAAAAACAAACAA  1050
     R  A  P  R  C  T  I  S  *

1051 TAAACGCTCTCGCTCTGGCACCCGATGACACGCCTCCGTTCTCTCTCTCCCTCCCCCATCCCCCCCATCCCCCCC  1125
       → IR
1126 GCGCGCCGCCGCCCCACGCGCGCCACGTCCTCCCTCCCCGCGGCCGCCCGCCCCCCCCCCTTGGCGCCATCCGAC  1200

1201 AGACTCGCGCCGCCGCCACCCACTCGCTCTCCCCCATTTCCCCCCCCCTTCCCCCCCGCTGCCCTGACGTCACTC  1275

1276 CCCCTTCCCACCAATAGCCGCCGAGGACCTCACCCCCCACTCCTTGCACCATCTCCTAGCCGCCGAGGACTCCCC  1350

1351 CGGACTCCCCCCACCAACAACTTTAACAATAAACGGCCTCGCTCTCGAACCCGACGCGCCCGGCCTCTGTCCTTT  1425

1426 CTCCCCCTCTCCCGTCCCACTCCCCTCTCCCCTCTCCCCCACCGTCCCCCCGTCCCCTCTCCCCCACCGTCCCC  1500
                                          DR                      DR
1501 CCGTCCCCCTCTCCCCCACCGTCCCCCCGTCCCCCTCTCCCCCACCGTCCCCCCGTCCCCTCTCCCCCACCGTC  1575
         DR                      DR                      DR
1576 CCCCCGTCCCCCTCTCCCCCACCGTCCCCCCGCGGGGGGGGGGTTCCGTCCCATCCCCCCGTCTCACTCCCCTCT  1650
               (DR)
1651 CCCTCCACCCCGTCTCATCCCCCGTCTCATCCCCCCATCTCCCTTCCCCACGAGGGCCGGGAGGGAAAAAACGCC  1725
```

DNA-sequence of the 28K gene

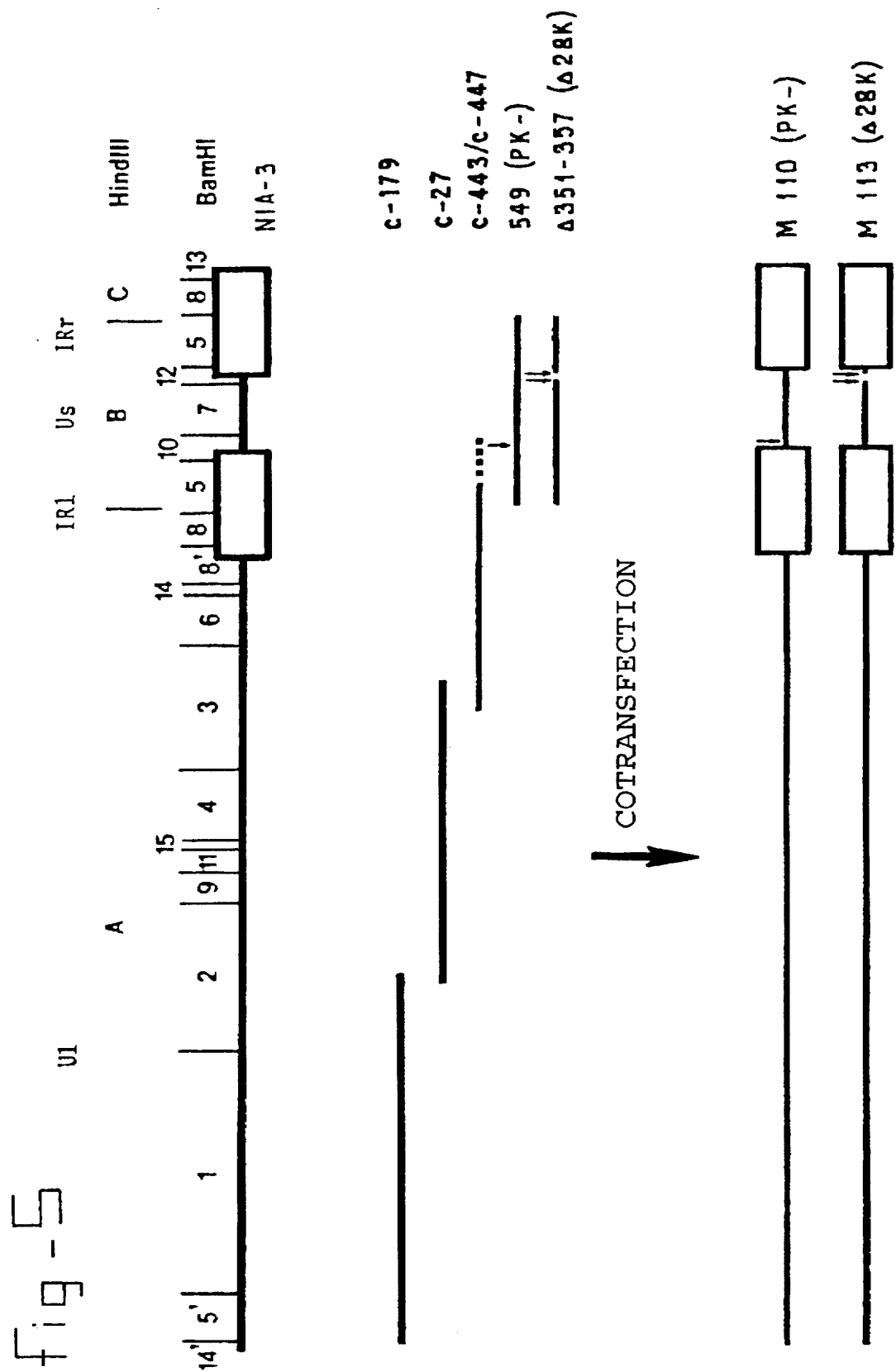

MUTANT PSEUDORABIES VIRUS, AND VACCINES CONTAINING THE SAME

This application is a continuation of application Ser. No. 07/834,569, filed Mar. 30, 1992, now abandoned.

The invention relates to a pseudorabies virus (PRV) not occurring in nature and having a genome possessing one or more mutations.

Pseudorabies is a disease of all domestic animals with the exception of the horse, and causes severe damage, especially in pigs and cattle. The pig is the natural host of pseudorabies virus, a herpesvirus which is also called Aujesky's disease virus. In pigs an infection with PRV may cause a disease of the respiratory organs and encephalitis and, eventually may lead to death.

Animals are infected by PRV via the nasal route. After an initial multiplication of the virus in the mucous membranes of the upper part of the respiratory and digestive tracts the virus spreads via the nerves to the brain. The severity of the infection may vary from acute to subclinical and is mainly dependent on the virulence of the virus and on the age of the infected animal.

In order to limit the economical damage caused by death and growth retardation of the infected animals vaccinations are carried out. For this purpose vaccines based on attenuated live virus and vaccines based on inactivated virus are available. Attenuated live virus vaccines are generally preferred as they may be prepared more easily and, therefore, are less expensive than inactivated virus vaccines.

The initially developed vaccines based on attenuated live virus had various disadvantages. Thus, generally, these vaccines were produced by serial passages of virulent strains in tissue cultures (50-900 passages) thereby inducing uncontrolled mutations in the virus. As a result, the composition of such vaccines was not homogeneous. The mixtures contained virus of variants of unknown virulence and of unknown protective power. Moreover, there was the risk of return to virulence with such vaccines.

The development of the techniques for the manipulation of genetical material has opened the possibility to obtain vaccines of attenuated live virus with avoidance of these disadvantages. The structure of the PRV genome is described in literature (Virology 97, 151-163 (1979)). The PRV genome contains about 150,000 nucleotide pairs. It contains two inverted repeats and two unique sequences, a short one and a long one, which are called Us and Ul. Based on the DNA sequence in question PRV has been classified as a D-herpesvirus.

The genome of the virulent PRV strain NIA-3 is given schematically in FIG. 1 which shows the restriction sites of HindIII and BamHI. The inverted repeats are shown as IRl and IRr. Also the long and short unique sequences, Ul and Us are shown.

J. gen. Virol. 68, 523-534 (1987) describes NIA-3 derived PRV deletion mutants. These mutants have a strongly reduced virulence, but still induce sufficiently high neutralizing antibody titers, due to which the mutants are suitable for use in vaccines. The deletions are situated in the MluI-BglII fragment of BamHI fragment 7. It has now become apparent that these mutations have caused defunctionalization of the genes coding for glycoproteins gI and gp63. The mutants described also possess deletions around the ends of HindIII fragment B, which deletions, taken alone, cause an only slightly lowered virulence.

BRIEF DESCRIPTION OF THE DRAWINGS

FIG. 1. Genome of the virulent PRV strain NIA-3.
FIG. 2. DNA sequence of the protein kinase (PK) gene.
FIG. 3. DNA sequence of the 28k gene.
FIG. 5. Construction of mutant viruses.

Figure 4A:
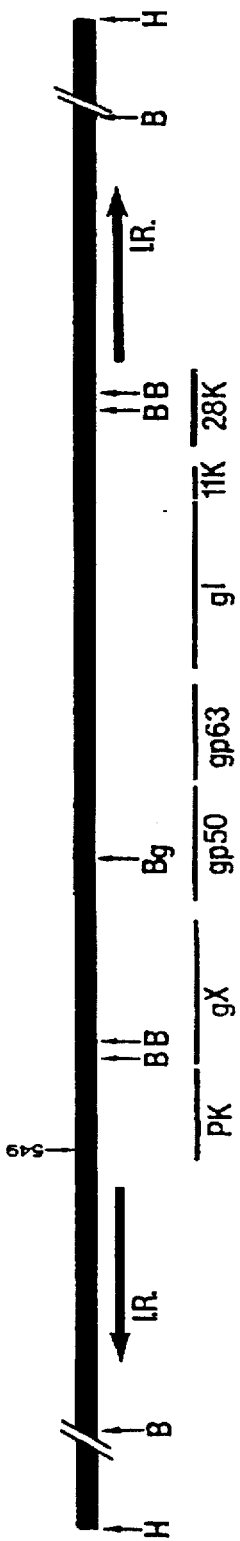
FIG. 4. Position of the seven genes in the Us region of PRV.

It was now found that PRV mutants having a genome which, in comparison with the genome of PRV of the wild type, have a protein kinase and/or 28K gene defunctionalized by genetical manipulation, are viruses capable of replication.

Further, it was found that PRV mutants the genome of which contains a defunctionalized protein kinase gene show a virulence which is lowered in comparison with strains of the wild type, and possess good immunogenicity. On the other hand, defunctionalization of the 28K gene has no detectable influence on the virulence and on the immunogenicity.

The fact that the protein kinase gene and the 28K gene of PRV do not have essential functions in the replication of the virus allows the introduction of advantageous mutations into the regions of these genes. Therefore, the invention relates to a pseudorabies virus not occurring in nature and having a genome possessing a mutation in the protein kinase gene region and/or in the 28K gene region, to vaccines containing such a virus, as well as to a process for preparing a vaccine for protection of pigs against pathogens, in which a pseudorabies virus according to the invention is formed into a pharmaceutical composition having immunizing properties.

A mutation is understood to be a change of the genetic information in the above-mentioned regions with respect to the genetic information present in these regions of the genome of naturally occurring pseudorabies virus. The mutation is, for example, a nucleic acid substitution, deletion, insertion or inversion, or a combination thereof. Especially, a pseudorabies virus according to the invention possesses a deletion and/or an insertion in one or in both of above-mentioned regions.

The protein kinase gene is localised in BamHI fragment 10, that is to say upstream of the sequence coding for glycoprotein gX. The sequence coding for the 28K protein lies downstream of the 11K gene (transition of BamHI fragment 7 to fragment 12).

The DNA sequence of the protein kinase (PK) gene has been determined and is given in FIG. 2. The start positions for the transcription are indicated therein by horizontal arrows. TATA box consensus sequences are underlined. IR means inverted repeat. The initiation codon of the gX gene is at position 1395.

The DNA sequence of the 28K gene is given in FIG. 3. The start position of the transcription is also indicated therein by a horizontal arrow. The TATA box consensus sequence is underlined. The poly-A-position has a double underlining. The inverted repeat is, again, indicated by IR. DR indicates a direct repeat (26 bp). The termination of the 11K gene is at position 7.

Figure 4B:
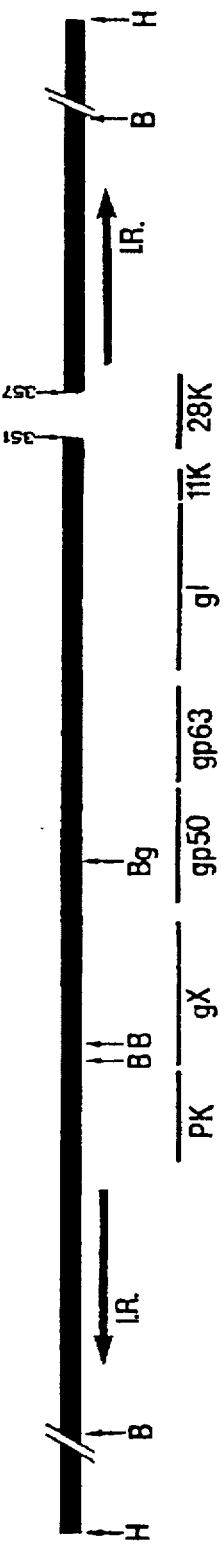

FIG. 4 shows the position of the seven genes in the Us region of PRV, as presently known. FIG. 4A describes schematically the HindIII fragment B of an insertion mutant having a defunctionalized PK gene which will be described further below. FIG. 4B schematically shows the HindIII fragment B of a deletion mutant having a defunctionalized 28K gene which will be described further below.

In FIG. 4 the restriction sites of BamHI have been indicated by B, those of BglII with Bg and those of HindIII with H.

The positions of the DNA sequences coding for PK and for the 28K protein have been determined as follows.

Protein kinase

The open reading frame (in the following indicated by ORF) of 1170 nucleotides upstream of gX lies entirely in the Us region (FIG. 2). In an in vitro transcription/translation experiment the presence of this ORF has been confirmed. Assuming that the first ATG codon at position 163 functions as translational start codon this yields a protein of 390 amino acids (43K). However, mRNA mapping experiments show that, probably, the third ATG codon at position 325 is the most important start of the translation. The protein would than have a length of 336 amino acids (37K).

As early as two hours after infection transcripts from this region can be detected in tissue cells infected with PRV. The 5'-end of these 2.7 kb mRNA's has been determined exactly by means of primer extension experiments. Two transcription start sites were found: more than 95% of the mRNA's start at position 258, 260 or 261 (with C, U or A, respectively), thereby coding for the 37K product. The remaining part of the mRNA's starts at position 99 (with A), thereby coding for the 43K product.

The protein contains conserved domains of a serine/threonine protein kinase (Science 241, 42–52 (1988)) and is homologous to the protein kinase coded by Us3 of herpes simplex virus type-1 (HSV-1) (J. Mol. Biol. 181, 1–13 (1985)). Therefore it is probable that this PRV protein is the 38K protein kinase (PRV-PK) found in PRV infected cells (Eur. J. Biochem. 152, 57–65 (1985) and Eur. J. Biochem. 167, 507–512 (1987)).

28K protein

The ORF of 768 nucleotides downstream of 11K encodes a protein of 256 amino acids (28K) (FIG. 3). The existence of this ORF has been confirmed in an in vitro transcription/translation experiment as well. The 28K protein is, to a low degree, homologous to the Us2 protein of HSV-1 (J. Mol. Biol. 1981, 1–13 (1985)).

As early as two hours after infection of tissue culture cells mRNA's specific for 28K are detectable. Five hours after infection the transcription level has increased considerably, however. The 5'-end of this 1.15 kb mRNA has been determined by means of primer extension experiments. The mRNA's start at position 146, 147, 148 or 149 (with C, A, C or A, respectively). FIG. 3 also shows a small part of the sequence of the inverted repeat. It contains five identical direct repeats of 26 bp (and a shorter one of 24 bp).

The regions of the PRV according to the invention in which a mutation may be present are characterized by a nucleic acid sequence containing the gene encoding the PK protein or 28K protein, as well as nucleic acid sequences at the 5' and 3' ends of these genes, whereby these flanking sequences do not encode a polypeptide. Consequently, the regions also comprise the sequences which are important for the regulation and expression of the genes involved.

According to the invention such a mutation may be present in the PK gene region and/or in the 28K gene region, which regions are characterized by nucleic acid sequence 1–1394, as depicted in FIG. 2, or by the nucleic acid sequence 7–1725 as depicted in FIG. 3, respectively.

Preferably, the mutation is present in the gene encoding the PK protein and/or in the gene encoding the 28K protein. A very suitable region for the insertion is nucleic acid sequence 163–1332 depicted in FIG. 2 and nucleic acid sequence 232–999 depicted in FIG. 3.

A suitable mutation is, for example, the insertion of a nucleic acid sequence of a gene derived from one or more pathogens found in pigs, but different from PRV. These are namely nucleic acid sequences containing genetical information relevant to the induction of a protective immune response. After vaccination of an animal with such a recombinant virus according to the invention the virus can multiply in the infected target cells, thereby liberating a large number of vector particles containing the foreign genetical information. Subsequently this virus, again, can infect target cells thereby starting a new multiplication round. The result is that larger dosages of the foreign gene product are offered to the immune system of the host than generally obtainable after vaccination with a subunit vaccine.

Although an insertion of a gene of a pathogen different from PRV may be present in the region of the protein kinase gene or in that of the 28K gene, or in both of these regions, the region of the 28K gone is preferred in case of insertion into the genome of a PRV strain suitable for use in vaccines, because defunctionalization of the nucleic acid sequences encoding the 28K gene has no influence on the replication, the virulence and the immunogenic power of the mutant PRV.

Preferably, the PRV vector, in the genome of which foreign nucleic acid sequences have been introduced into the 28K gene and/or into the protein kinase gene, is a PRV attenuated by a deletion in the glycoprotein gI gene and/or in the thymidine kinase gene.

Insertion of foreign nucleic acid sequences may be effected at any desirable site within the above-mentioned regions, whereby the PK gene and/or the 28K gene may be deleted entirely or partially.

The genetical information considered for insertion into a PRV vector may be derived, for example, from viruses, such as hog cholera virus, parvovirus, transmissible gastroenteritis virus, porcine endemic diarrhoea virus and influenza virus, or from bacterial pathogens, such as *Pasteurella multocida, Bordetella bronchiseptica, Actinobacillus pleuropneumoniae, Streptococcus suis. Treponema hyodysenteria, Escherichia coli* and Leptospira, or from Mycoplasmata, such as *M. hyopneumoniae* and *M. lyorhinis* etc.

The techniques of cloning nucleic acid sequences of pathogens in PRV subgenomic fragments and subsequently integrating these in the genome of a PRV are generally known. By way of example, in this connection reference is made to the method using the regeneration of recombinant PRV from subgenomic fragments described by M. van Zijl et al. in J. Virol. 62, 2191–2195 (1988).

In the investigation of the influence of the defunctionalization of the PRV protein kinase and 28K gene, respectively, upon the replication and the virological properties, the genomic regions involved were mutated by an insertion of an oligonucleotide having translational stop signals and, moreover, comprising a restriction site for an enzyme, which restriction site is not present in NIA-3. The oligonucleotide used has the formula

5'-TAGGCTAGAATTCTAGCCTA-3'

3'-ATCCGATCTTAAGATCGGAT-5'

This oligonucleotide comprises three translational stop codons, TAG, in each of the possible three reading frames, and in both directions. Moreover, it contains an EcoRI recognition site, GAATTC, and further, the oligonucleotide is a palindrome. Insertion of this double-stranded oligonucleotide into any gene encoding a protein, in any orientation, in any reading frame leads to termination of the translation of the mRNA of that gene. The presence of the EcoRI recognition site (which is not present in the NIA-3 genome) in the oligonucleotide facilitates the determination of the insertion site of the oligonucleotide, as well as further manipulation of the clone in which the oligonucleotide has been inserted.

The above-mentioned oligonucleotide may be obtained in a known way by synthesis by means of the fosforamidite method.

In the following the construction and the biological properties of some mutants according to the invention are described in detail.

1. Construction of a clone of HindIII fragment B of PRV strain NIA-3.

A derivative of plasmid vector pBR322 was constructed in which the EcoRI site was deleted by treatment with the Klenow fragment of DNA polymerase I in the presence of dATP and dTTP. The 27 kbp HindIII fragment B of PRV strain NIA-3 (FIG. 1) was cloned in the HindIII site of the latter vector.

2. Linearisation of the clone at quasi-random sites.

Covalently closed circular DNA (25 µg) of the HindIII-B clone was partially digested by incubation, during 15 minutes at a temperature of 37° C., in the presence of, in each case, one of the following restriction enzymes: FnuDII, HaeIII and RsaI. The digestions were carried out in a solution having a volume of 125 µl and containing the DNA together with either 2 U FnuDII in 20 mM Tris-HCl, pH 7.5, 8 mM $MgCl_2$, 50 µg ethidium bromide (EtBr), or together with 1 U HaeIII in 20 mM Tris-HCl, pH 7.5, 50 mM NaCl, 8 mM $MgCl_2$, 5 µg/ml EtBr, or together with 0.5 U RsaI in 20 mM Tris-HCl, pH 7.5, 50 mM NaCl, 8 mM $MgCl_2$, 0.5 µg/ml EtBr.

These partial digestions resulted in the formation of about 30% linear full-length DNA fragments, as judged by means of agarose gel electrophoresis. As the restriction enzymes used have recognition sites scattered throughout the entire DNA fragment, this fraction can be considered to be linearized at quasi-random sites within the clone. This linear DNA was purified by centrifugation in a density gradient of cesium chloride (EtBr) for elimination of undigested closed circular DNA, followed by preparative agarose gel electrophoresis for elimination of molecules having single strand cuts and of molecules having been cut more than once.

3. Insertion of the oligonucleotide into the linearized HindIII-B clone.

Of each of these 3 partial digestions 1 µg of the linearized DNA was ligated with 0.03 µg of the kinase treated oligonucleotide (a 50-fold molar excess) in a volume of 15 µl. Concatemers of ligated HindIII-B fragment and oligonucleotides were digested with EcoRI to form full-length fragments having oligonucleotide halves at each end. These fragments were isolated by preparative agarose gel electrophoresis and electroelution. Then the three DNA preparations resulting from the three partial digestions were combined. Of this DNA 0.5 µg was recircularized by ligation of the half EcoRI recognition sites at both ends of the linear HindIII-B fragments, in a volume of 400 µl. DNA was precipitated from this ligation mixture and dissolved in 10 µl 10 mM Tris-HCl, pH 7.5, 1 mM EDTA. *E. coli* strain DH5 was transformed with this DNA thereby using the method of Hanahan (DNA Cloning, a Practical Approach, I.R.L. Press Ltd., U.K., vol. 1, pages 119–135 (1985)). This resulted in a series of mutant HindIII-B clones each having the oligonucleotide inserted at a quasi-random site.

4. Analysis of the recombinant clones.

The integrity of the recombinant clones was examined by means of digestion with restriction enzymes BamHI and HindIII, followed by agarose gel electrophoresis. The insertion site of the oligonucleotide in each of these recombinant clones was determined by means of double digestions with restriction enzymes BamHI+EcoRI and BglII+EcoRI, followed by agarose gel electrophoresis.

5. Reconstruction of mutant pseudorabies virus.

Cloning of vital subgenomic fragments in the cosmid vector pJBF and regeneration of PRV from subgenomic fragments was carried out as described by Van Zijl et al., J. Virol. 62, 2191–2195 (1988). Cloning of the Us containing HindIII-B fragment of PRV strain NIA-3 was described by Quint et al., J. Gen. Virol. 68, 523–534 (1987).

In order to obtain the vital inserts free from vector sequences the cosmid DNA was digested with EcoRI, and the plasmid DNA was digested with HindIII, followed by purification of the vital inserts by glycerol gradient centrifugation. The viral inserts from the cosmid clones C-179, C-27 and C-443, as well as the HindIII fragment B were used for the construction of the wild type PRV cosNIA-3. These combined fragments contain the complete genetical information of PRV.

For the construction of the mutant viruses, cosmid clones C-179, C-27, as well as either C-443 for the construction of the Δ28K mutant, or C-447 (cosmid having a deletion of 8 kbp due to which the overlap with the HindIII fragment B is reduced) for the construction of the PK mutant and, finally, the mutant HindIII fragments B were used.

In FIG. 5 these constructions are shown schematically in relation to the restriction map of NIA-3. The vertical arrows indicate the insertion sites of the oligonucleotide.

Co-transfection of PK15 cells with these fragments gave, after in vivo homologous recombination between the overlapping ends of the fragments, infectious virus having the introduced mutation in the HindIII fragment B. Mutant virus obtained in this way was subjected three times to plaque purification in SK6 cells. Then DNA was isolated from the SK6 cells infected with these mutants, followed by digestion of this DNA with BamHI and BamHI+EcoRI. These DNA preparations, as well as DNA isolated from NIA-3 infected cells and digested in the same way, were analyzed by agarose electrophoresis.

6. Construction of NIA-3 PK⁻ and Δ28K mutants.

Using the above-described technique the mutant virus M110 (PK⁻) was obtained by recombination of fragments C-179, C-27, C-447 and HindIII-B clone 549 having an insertion in the translation termination oligonucleotide in the 5'-end of the protein kinase gene (FIG 4A). The presence of the oligonucleotide causes an early termination of the translation of the PK⁻ mRNA. The integrity of the oligonucleotide and of the flanking vital DNA sequences, as well as the exact position of the insertion of the oligonucleotide within the PK gone were determined by DNA sequence analysis using the method of Sanger and Coulson (Proc. Natl. Acad. Sci. USA 74, 5463–5467 (1977)). For this purpose, DNA of the HindIII-B clone 549 was digested with the restriction enzymes SaU3A+EcoRI and inserted into the vector M13 mp11 which had been digested with BamHI+EcoRI. Sequence analysis of this recombinant plasmid revealed that there were no deletions on either side of the insertion site of the oligonucleotide. The insertion site of the oligonucleotide was between base pairs 457 and 458 with respect to the 5'-end of the PK transcript as shown in FIG. 2A by a vertical arrow.

In a second experiment the reconstruction of the PRV PK⁻ insertion mutant was repeated. The experiment was carried out as described above. This resulted in mutant virus M119 (PK⁻).

Oligonucleotide insertion mutagenesis of the HindIII-B fragment also yielded two clones having the oligonucleotide inserted at two positions in the 28K gone (HindIII-B-351 and 357). These were used to obtain a mutant in which the 28K gene is deleted for the greater part. For this purpose the mutant HindIII-B fragment 351 as well as fragment 357 were digested with BglII+EcoRI. Both enzymes cut once in these clones (BglII in the gp50 gene and EcoRI in the inserted oligonucleotide, FIG. 4B), resulting in two DNA fragments after digestion. The 4.9 kbp BglII-EcoRI fragment of the mutant clone 357 was replaced with the 4.4 kbp BglII-EcoRI fragment of clone 351 resulting in a mutant HindIII-B fragment having a deletion of about 0.5 kbp between the oligonucleotide insertion sites of 351 and 357. This results in deletion of the greater part of the 28K gene (FIG. 4B). Using the technique described under 5 a mutant virus further designated strain M113 (Δ28K) was obtained with clone 351-357.

7. Growth of PK⁻ and 28K mutants in tissue culture cells.

In SK6 cells, the 28K mutant PRV strain showed a growth comparable to that of NIA-3. The PK⁻ mutant had a slower growth than NIA-3.

Pathogenicity and immunogenicity

Description of the experiments

In experiments 1 and 2 the pathogenicity and immunogenicity of the insertion mutants M110 (PK⁻) and of the deletion mutant M113 (Δ28K) were examined in 10 week old piglets which were free from antibodies to PRV. $10^5$ PFU was administered intranasally. Groups consisted of 8–9 piglets. In experiment 1 mutant M110 was examined, in experiment 2 mutant M113. In each experiment there were two control groups, that is to say a group (C) infected with strain M209 (cosNIA-3) and an uninfected group (A). Eight weeks after inoculation all of the piglets were infected with strain NIA-3 so as to determine the immunogenicity. The 18 weeks old, uninfected group (A) was used as control.

Strain M209 (cosNIA-3) is a virulent PRV regenerated from cosmid fragments C-179, C-27, C-443 and the HindIII-B fragment of NIA-3.

In experiment 3 the pathogenicity of M119 (PK⁻) was investigated in 3 weeks old piglets free from antibodies to PRV. Also tested was the pathogenicity of PRV PK⁺(M120) which virus was obtained after repair of the defect in the PK gene of M119 (PK⁻). This rescue was effected by cotransfection, in SK-6 cells, of M119 virus DNA and BamHI fragment 10 of NIA-3 virus DNA. BamHI fragment 10 overlaps the PK gene. If the insertion of the PK gene is the only cause of the pathogenicity reduction described in experiment 1, rescue of the PK gene will have to lead to a virus, M120 (PK⁺) having the virulence properties of the control strain M209 (cosNIA-3). The test groups A, B and C consisted in each case of five 3 weeks old SPF piglets free from antibodies to PRV. The piglets of groups A, B and C were infected intranasally with $10^5$ PFU of virus strains M118 (PK⁻), M120 (PK⁺), and M209 (cosNIA-3), respectively.

Pathogenicity

Results of experiments 1 and 2

After "vaccination" with M209 (cosNIA-3) the normal clinical symptoms such as no or strongly reduced appetite, lethargy, vomiting, sneezing, nasal excretion and fever were observed. Some of the animals also showed neurological phenomena at the moment of observation. In both of the experiments 2 of the 6 animals died. The following table summarizes the virulence data.

TABLE A

| Group | | N.S.*) | Mortality | MTD | Weight increase (kg) day 18–day 1 |
|---|---|---|---|---|---|
| Experiment 1. | | | | | |
| A | Control | − | 0/6 | | 12.5 |
| B | M110 (PK⁻) | − | 0/7 | | 12.0 |
| C | M209 (cosNIA-3) | + | 2/6 | 8.0 | 4.6 |
| Experiment 2. | | | | | |
| A | Control | − | 0/6 | | 13.8 |
| B | M113 (Δ28K) | + | 5/7 | 7.4 | −4.0 |
| C | M209 | + | 2/6 | 10.0 | 6.1 |

*)Neurological symptoms (ataxy, paralysis, tremor)

In the group inoculated with mutant M110 (PK⁻) the clinical symptoms after vaccination remained limited to lethargy, loss of appetite in some animals and increase of body temperature. The body temperatures observed after inoculation with M110 (PK⁻) were clearly lower than after infection with M209 (cosNIA-3). Serious symptoms of disease, among which neurological symptoms, occurred after infection with strain M113 (Δ28K). In the M113 group 5 out of 7 piglets died. Three died on day 7 and two on day 8. Of the remaining piglets one remained chronically ill. The main weight increase of the group infected with M110 (PK⁻) was comparable with that of the uninfected control group A. This is in agreement with the mild clinical findings after inoculation with this mutant.

Weight loss was observed after infection with mutant M113 (Δ28K). The weight curve of the M113 group is the resultant of the weight curves of the two piglets which had survived after infection. One of these piglets remained chronically ill and its weight gradually decreased. The other piglet's weight increased again beginning on day 9 after infection.

A reduction of the amount of excreted virus was observed after inoculation with M110 (PK⁻).

Four days after inoculation 2 piglets from each group were killed and various tissues/organs (a total of 19 per piglet) were sampled for virus isolation. A summary of the results is given in table B.

Thus, the results show that, in 10 weeks old pigs, strain M110 (PK⁻) shows a virulence which is considerably reduced as compared with the parent virus. In contrast, strain M113 (Δ28K) has a virulence comparable with that of the parent strain.

TABLE B

| Virus replication in organs (4 days after inoculation) | | | |
|---|---|---|---|
| Group | Nasopharyngeal area | C.N.S. | Lung |
| Experiment 1. | | | |
| B  M110 (PK⁻) | + | + | + |
| C  M209 (cosNIA-3) | + | + | + |
| Experiment 2. | | | |
| B  M113 (Δ28K) | + | + | + |
| C  M209 (cosNIA-3) | + | + | + |

Results of experiment 3

After intranasal inoculation of the 3 weeks old seronegative piglets in group C with M209 (cosNIA-3), clinical symptoms characteristic of a virulent PRV infection were observed. These were not only general symptoms of illness, such as fever—the mean body temperature of the group was higher than 40° C. during 6 days—, decreased appetite, lethargy, vomiting, sneezing, nasal excretion, but also neurological symptoms, such as convulsions, tremors, coordination disorders and paralytical symptoms. Four of the 5 inoculated piglets died of pseudorabies on day 6, 6, 7, and 7, respectively (mean time to death 6.5 days). The piglets of group B which were infected with M120 (PK$^+$) showed the same general and neurological symptoms as were observed in group C. In group B 3 of the 5 infected piglets died of pseudorabies on day 6, 7, and 12, respectively (mean time to death 8.3 days). In group A which was infected with M119 (PK$^-$) only mild general symptoms of illness were observed on day 3 and day 4 after inoculation: the 5 piglets had a mean body temperature higher than 40° C., and one piglet was lethargic on day 5 after inoculation. Loss of apetite was not observed, and the weight increase between day 1 and day 18 was not changed in comparison with that of control piglets.

Piglets in groups A, B, and C shed virus in the saliva from day 1 up to and inclusive of day 9 after infection. The average amount of virus observed between days 1 and 9 in the oropharyngeal swabs of the piglets of each group did not show large differences either.

Immunogenicity

Results of experiment 1

Piglets "vaccinated" with M110 (PK$^-$) and M209 (cosNIA-3) were shown to be very well protected against a challenge infection with NIA-3, 8 weeks after "vaccination". Growth retardation, clinical symptoms, significant increase of body temperature and reduction of food intake were not observed. The control piglets gave, after challenge, the normal clinical symptoms, such as decreased appetite, lethargy, vomiting, sneezing, nasal excretion and fever. All of the control piglets survived the challenge infection. The growth retardation of the control piglets was 15 days. It is remarkable that piglets vaccinated with mutant virus M110 (PK$^-$) shed virus during 7 days after challenge. The very high neutralizing antibody titers (higher than 1000) in the blood reduced the period and the level of virus shedding, but were unable to prevent the latter completely. The virus replication observed was confirmed by the increase of serum neutralization titer after challenge.

We claim:

1. An attenuated pseudorabies virus not occurring in nature and having a genome containing at least one mutation selected from a mutation in the protein kinase region and an insertion in the 28K region, the virus being attenuated in that it does not produce at least one of functional gI protein, functional thymidine kinase and protein kinase.

2. The pseudorabies virus according to claim 1, wherein said mutation in the protein kinase region is selected from the group consisting of a deletion, an insertion, and combinations thereof.

3. The pseudorabies virus according to claim 1, wherein the genome of said virus contains a nucleic acid sequence encoding an antigenic polypeptide of a pathogen found in pigs.

4. The pseudorabies virus according to claim 3, wherein said nucleic acid sequence encoding said polypeptide being contained in said 28K region.

5. The pseudorabies virus according to claim 1, wherein said virus is derived from strain NIA-3.

6. Vaccine for protecting pigs against pseudorabies, containing a pseudorabies virus according to claim 1 in combination with a biologically acceptable carrier.

7. A process for preparing a vaccine for protecting pigs against pseudorabies, comprising combining a pseudorabies virus according to claim 1 with a biologically acceptable carrier.

8. A process for producing a recombinant attenuated pseudorabies virus comprising introducing into the protein kinase region of said virus at least one mutation selected from deletions, insertions and substitutions, said at least one mutation altering the amino acid sequence of the polypeptide encoded by the coding region of said protein kinase region when said mutation is introduced in said coding region, and said at least one mutation reducing the virulence of the virus compared to the parent virus.

9. The process according to claim 8, further comprising introducing a deletion in at least one gene of said virus selected from the group consisting of the thymidine kinase gene and gI gene.

10. A process of producing a recombinant attenuated pseudorabies virus capable of expressing an antigenic polypeptide of a pathogen found in pigs, said pathogen differing from pseudorabies virus, said process comprising introducing into the protein kinase region of said virus a nucleotide sequence encoding said antigenic polypeptide.

11. The process according to claim 10, further comprising introducing a deletion in at least one gene of said virus selected from the group consisting of the thymidine kinase gene and gI gene.

12. A process of producing a recombinant attenuated pseudorabies virus expressing an antigenic polypeptide of a pathogen found in pigs, said pathogen differing from pseudorabies virus, the process comprising introducing at least an attenuating mutation in the genome of the virus and introducing into the 28K protein region of the virus a nucleotide sequence encoding said antigenic polypeptide.

13. The process of claim 12, wherein the attenuating mutation is a deletion in at least one member of the group consisting of the protein kinase gene, thymidine kinase gene and gI gene of said virus.

* * * * *